(12) United States Patent
Yang et al.

(10) Patent No.: US 8,889,929 B2
(45) Date of Patent: Nov. 18, 2014

(54) PROCESS TO MAKE 1,1,2,3-TETRACHLOROPROPENE FROM 1,1,3-TRICHLOROPROPENE AND/OR 3,3,3-TRICHLOROPROPENE

(71) Applicant: Honeywell International Inc., Morristown, NJ (US)

(72) Inventors: Terris Yang, East Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/181,769

(22) Filed: Feb. 17, 2014

(65) Prior Publication Data

US 2014/0235906 A1    Aug. 21, 2014

Related U.S. Application Data

(60) Provisional application No. 61/766,405, filed on Feb. 19, 2013.

(51) Int. Cl.
*C07C 17/25* (2006.01)
*C07C 17/04* (2006.01)

(52) U.S. Cl.
CPC ............... *C07C 17/04* (2013.01); *C07C 17/25* (2013.01)
USPC ........................................................ 570/227

(58) Field of Classification Search
CPC ...................................................... C07C 17/25
USPC ........................................................ 570/227
See application file for complete search history.

(56) References Cited

U.S. PATENT DOCUMENTS

| | | |
|---|---|---|
| 3,926,758 A | 12/1975 | Smith |
| 4,535,194 A | 8/1985 | Woodard |
| 4,650,914 A | 3/1987 | Woodard |
| 5,689,020 A | 11/1997 | Boyce |
| 8,115,038 B2 | 2/2012 | Wilson et al. |
| 8,258,355 B2 | 9/2012 | Merkel et al. |
| 2009/0216055 A1 | 8/2009 | Wilson et al. |
| 2012/0035402 A1 | 2/2012 | Wilson et al. |
| 2012/0065434 A1 | 3/2012 | Nose et al. |
| 2012/0289751 A1 | 11/2012 | Nose et al. |
| 2013/0012743 A1 | 1/2013 | Wilson et al. |

FOREIGN PATENT DOCUMENTS

WO    2011110889 A1    9/2011

OTHER PUBLICATIONS

PCT ISR & Written Opinion issued in PCT/US2014/016873 dated Jun. 8, 2014.

*Primary Examiner* — Elvis O Price
(74) *Attorney, Agent, or Firm* — Bruce O. Bradford

(57) ABSTRACT

Disclosed is a process for the synthesis of 1,1,2,3-tetrachloropropene (HCC-1230xa) using 1,1,3-trichloropropene (HCC-1240za) and/or 3,3,3-trichloropropene (HCC-1240zf) and $Cl_2$ gas as the reactants, wherein the process takes place in a single reactor system. Before this invention, HCC-1230xa was made in a two-step process using HCC-1240za/HCC-1240zf and $Cl_2$ gas, and the processing was conducted using two separate reactors.

10 Claims, 1 Drawing Sheet

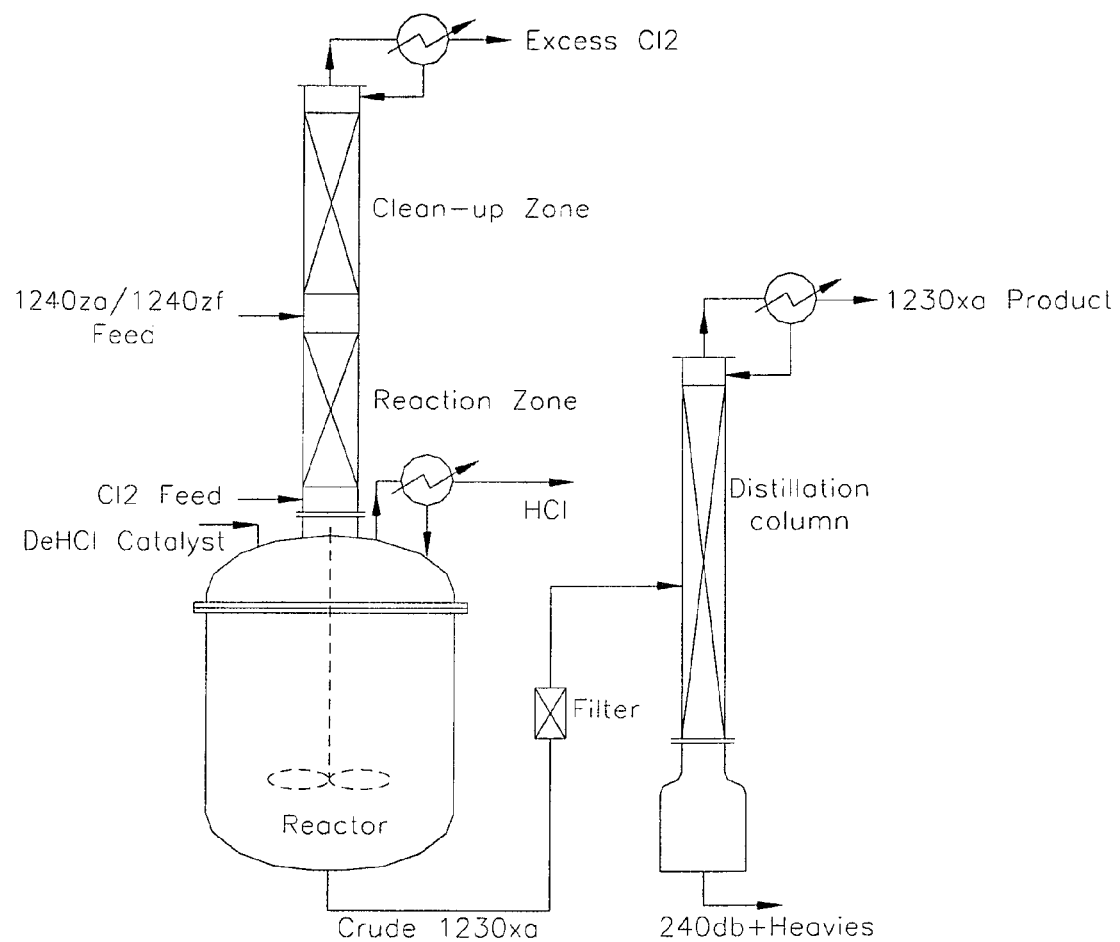

PROCESS TO MAKE 1,1,2,3-TETRACHLOROPROPENE FROM 1,1,3-TRICHLOROPROPENE AND/OR 3,3,3-TRICHLOROPROPENE

CROSS-REFERENCE TO RELATED APPLICATION

This application claims benefit of U.S. Provisional Patent Application Ser. No. 61/766,405 filed Feb. 19, 2013, the disclosure of which is hereby incorporated herein by reference.

BACKGROUND OF THE INVENTION

As disclosed in U.S. Pat. No. 8,058,486, the compound 1,1,2,3-tetrachloro-propene (HCC-1230xa) is an important precursor that can be used for the production of 2,3,3,3-tetrafluoropropene (HFO-1234yf), which is a low GWP molecule that can be used as an effective refrigerant, fire extinguishing agent, heat transfer medium, propellant, foaming agent, blowing agent, gaseous dielectric agent, sterilant carrier, polymerization medium, particulate removal fluid, carrier fluid, buffing abrasive agent, displacement drying agent and power cycle working fluid, to name but a few.

In normal practice, HCC-1230xa can be made in a two-step process using 1,1,3-trichloropropene (HCC-1240za or 1240za) and/or 3,3,3-trichloropropene (HCC-1240zf or 1240zf) as the starting material. In the first step, 1240za and/or 1240zf are chlorinated by $Cl_2$ in one reactor to form the intermediate product 1,1,1,2,3-penta-chloropropane (HCC-240db or 240db) under certain reaction conditions:

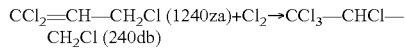

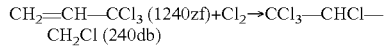

Next, the 240db is fed into another reactor and dehydrochlorinated by a catalyst (such as $FeCl_3$) to form HCC-1230xa and HCl:

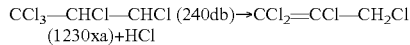

The present invention improves this two-reactor process by consolidating these two reactions into a single reactor, thus saving capital costs, simplifying the operation and improving both reaction times and product yield.

SUMMARY OF THE INVENTION

The process described herein combines two reactions for the formation of HCC-1230xa into one reactor, which will reduce the operational steps from two to one. The present invention consolidates the two-step process into one reactor which can significantly simplify the operation, and reduce both the operation and maintenance costs.

Thus, one embodiment of the invention is directed to a process for the synthesis of HCC-1230xa using HCC-1240za and/or HCC-1240zf and $Cl_2$ gas as the reactants with a dehydrochlorination catalyst, such as an iron halide catalyst or an equivalent, wherein the process takes place in a single reactor system.

In certain embodiments, the process is conducted in a single reactor system which comprises a continuous stirred-tank reactor (CSTR) equipped with a total condenser, combined with a reaction column and a total condenser.

In certain embodiments, the reaction column can be separated into four zones comprising (a) a $Cl_2$ feed zone, (b) a reaction zone, (c) an organic feed zone and (d) a clean-up zone. In certain embodiments, the starting material containing 1240za and/or 1240zf is fed into the reaction column via the organic feed zone. In certain embodiments, the $Cl_2$ gas is fed into the reaction column via the $Cl_2$ feed zone. In certain embodiments, the material used to build the reaction column comprises a chlorine-resistant material. In certain embodiments, the reaction column can be empty. In certain embodiments, the reaction column can be packed with chlorine-resistant material or equipped with trays/plates or a stirring device to enhance gas/liquid contact.

It should be appreciated by those persons having ordinary skill in the art to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

FIG. 1 shows a schematic of one embodiment of a single reactor design, useful in this invention for the production of HCC-1230xa.

DETAILED DESCRIPTION OF THE INVENTION

As shown in FIG. 1, the process of this invention is carried out in an apparatus including a CSTR (equipped with a total condenser) which connects to a reaction column equipped with a total condenser, and a distillation column. The reaction column can be separated into four zones, i.e., from the bottom to top, (1) a $Cl_2$ feed zone, (2) a reaction zone, (3) an organic feed zone and (4) a clean-up zone, as shown in FIG. 1.

During the operation, the starting material (1240za and/or 1240zf) is fed into the organic feed zone of the reaction column and flow downward via a liquid distributor, while an excess amount of $Cl_2$ gas is fed into the $Cl_2$ feed zone of the reaction column and flow upward via a gas distributor. Downward flowing 1240za/1240zf reacts with reversed flow of $Cl_2$ gas in the reaction zone to produce 1,1,1,2,3-pentachloropropane (HCC-240db). Un-reacted $Cl_2$ moves further up and continues to react with 1240za/1240zf in the vapor phase and/or in the liquid phase in the clean-up zone. Excess $Cl_2$ gas with organic vapor containing 1240za/1240zf and 240db passes through the total condenser, where 1240za/1240zf and 240db are condensed and returned back into the top of the reaction column as reflux. Excess $Cl_2$ is captured by a downstream scrubber.

HCC-240db produced in the reaction column moves downwards into the CSTR and is dehydrochlorinated to HCC-1230xa there by a dehydrochlorination catalyst (such as $FeCl_3$) at a controlled reaction temperature, residence time and $FeCl_3$/240db ratio. HCl and the organic vapor containing mainly HCC-240db and HCC-1230xa produced in the CSTR pass through the total condenser, where the organic vapor is condensed and returned back into the reactor and HCl is either captured as a byproduct or neutralized by a downstream scrubber.

The crude HCC-1230xa product is continuously discharged from the bottom of the CSTR, with the $FeCl_3$ catalyst removed by filtration, and fed into the distillation column, where the un-reacted intermediate HCC-240db and other high boiling compounds are separated as heavies and HCC-1230xa collected from the top of the column as the final product.

EXAMPLE 1

A jacketed Monel pipe (namely, Reaction Column or Pipe Reactor) with 1-inch ID and 28-inch long is connected to a 1000 ml round-bottom glass flask via a RCV valve. The pipe reactor can be either heated by steam or cooled by cooling water via the jacket side to control the reaction temperature. The pipe reactor is packed with structured PFA packing (20 inches in length), and equipped with a water-cooled total condenser. An organic feed line (located at 16 inches above the bottom of the pipe reactor) is connected to the 1240za supply container to feed the organic into the pipe reactor. Two inches above the organic feed port, an organic recycle line with a liquid seal loop is connected to a 2000 ml glass receiver to maintain a maximum liquid level of 18 inches inside the pipe reactor. The 1000 ml round-bottom glass flask is equipped with an agitator (namely, CSTR) and a water-cooled total condenser, and heated by an oil bath.

At the start-up, after the pipe reactor is filled with about 240 g of 1240za (>99.5 wt %), the pipe reactor is heated up to 80° C. by 30# steam. $Cl_2$ is fed into the pipe reactor via the $Cl_2$ dispenser located at the bottom of the pipe reactor. When the pipe reactor temperature starts to rise, the steam supply to the pipe reactor jacket is switched to cooling water to control the pipe reactor temperature at 80±5° C. The $Cl_2$ feed rate is controlled via a mass flow meter so that a total of 139 g of $Cl_2$ (about 120 mol % of 1240za) is fed into the pipe reactor in about 4 hours. Thereafter, continuous 1240za and $Cl_2$ feeds are started at flow rates of about 60 g/hr and about 12 std. L/hr for 1240za and $Cl_2$ respectively. At the same time, the generated 240db in the pipe reactor is transferred into the CSTR via RCV valve, with the transfer rate being controlled in such a way that the liquid level in the pipe reactor is stable (indicated by a side tube installed between organic feed and recycle ports). After 4 hours, the feeds to the pipe reactor and the transfer of 240db from the pipe reactor to CSTR are stopped, and the CSTR is agitated and heated to 120° C. After the CSTR temperature reaches 120° C., 3.5 g of anhydrous $FeCl_3$ is added into the CSTR via the $FeCl_3$ loading port, which initiates the 4 hours of batching of the material in the CSTR. After 4 hours, the CSTR is well batched, and a continuous operation is resumed by restarting 1240za and $Cl_2$ feeds into the pipe reactor, and 240db transfer from the pipe reactor to the CSTR at previous rates. The crude product of 1230xa is continuously pumped off the CSTR at a rate of about 74 g/hr and filtered for further purification. 1.7-2.2 g of anhydrous $FeCl_3$ is added into the CSTR every two hours to maintain the concentration of $FeCl_3$ in the range of 1.0-1.2 wt % in the CSTR.

EXAMPLE 2

This example uses the same apparatus as described in Example 1. At the start-up, the pipe reactor is filled with about 280 g of 240db (>99 wt %) and the CSTR is filled with 350 g of 240db (>99 wt %). The CSTR is agitated and heated to 120° C. After the CSTR temperature reaches 120° C., 3.5 g of anhydrous $FeCl_3$ is added into the CSTR via the $FeCl_3$ loading port, which initiates the 4 hours of batching of the material in the CSTR. Twenty minutes before the end of 4 hour batching, the pipe reactor is heated up to 80° C. by 30# steam and ready for continuous operation. After 4 hours, the material in the CSTR is well batched, the continuous operation begins by: Initiating feeds to the pipe reactor at flow rates of about 60 g/hr and about 12 std. L/hr for 1240za and $Cl_2$, starting 240db transfer from the pipe reactor to the CSTR at a rate that maintains the liquid level in the pipe reactor stable, and pumping off the crude 1230xa from the CSTR at a rate of about 74 g/hr.

During the operation, the temperature in the pipe reactor is maintained at 80±5° C., and the temperature in the CSTR is maintained at 120±2° C. The crude 1230xa product off the CSTR is filtered for future purification. 1.7-2.2 g of anhydrous $FeCl_3$ is added into the CSTR every two hours to maintain the concentration of $FeCl_3$ in the range of 1.0-1.2 wt % in the CSTR.

For the examples described herein, the liquid transferred from the pipe reactor into the CSTR usually contains the following components: 1240za: 0-0.5 wt %, 1230xa: 1.0-2.0 wt %, 240db: 96.5-98.5 wt %, 230da/230ab: 0.2-0.5 wt %, balanced with other impurities. The crude 1230xa product flow from the CSTR contains the following components: 1230xa: 97.5-98.5 wt %, 240db: 0.5-1.0 wt %; 230da/230ab: 0.2-0.5 wt %, 1230xa dimers: 0.1-0.5 wt %, balanced with other impurities.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the synthesis of 1,1,2,3-tetrachloropropene (HCC-1230xa) using an organic starting material selected from 1,1,3-trichloropropene (HCC-1240za), 3,3,3-trichloropropene (HCC-1240zf), or mixtures thereof, and $Cl_2$ gas as the reactants, with a dehydrochlorination catalyst, wherein the process takes place in a single reactor system.

2. The process of claim 1, wherein the dehydrochlorination catalyst comprises one ore more iron halide compounds.

3. The process of claim 2, wherein the iron halide compounds comprise one or more chloride compounds.

4. The process of claim 3, wherein the catalyst comprises $FeCl_3$.

5. The process of claim 1, wherein the single reactor system comprises a CSTR equipped with a total condenser, a reaction column and a total condenser.

6. The process of claim 5, wherein the reaction column can be separated into four zones comprising (a) a $Cl_2$ feed zone, (b) a reaction zone, (c) an organic feed zone and (d) a clean-up zone.

7. The process of claim 6, wherein the starting material containing 1,1,3-trichloropropene (HCC-1240za) or 3,3,3-trichloropropene (HCC-1240zf) or a mixture thereof, is fed into the reaction column via the organic feed zone.

8. The process of claim 6, wherein the $Cl_2$ gas is fed into the reaction column via the $Cl_2$ feed zone.

9. The process of claim 6, wherein the reaction column can be empty.

10. The process of claim 6, wherein the reaction column can be packed with chlorine-resistant material or equipped with trays/plates or stirring device to enhance gas/liquid contact.

* * * * *